(12) United States Patent
Murashko, Jr.

(10) Patent No.: US 8,641,741 B2
(45) Date of Patent: Feb. 4, 2014

(54) BONE PLATE AIMING BLOCK

(75) Inventor: Alexander Murashko, Jr., Shrewsbury, NJ (US)

(73) Assignee: Stryker Leibinger GmbH & Co. KG (DE)

( * ) Notice: Subject to any disclaimer, the term of this patent is extended or adjusted under 35 U.S.C. 154(b) by 0 days.

(21) Appl. No.: 13/878,838

(22) PCT Filed: Oct. 13, 2010

(86) PCT No.: PCT/US2010/052425
§ 371 (c)(1),
(2), (4) Date: Jun. 10, 2013

(87) PCT Pub. No.: WO2012/050572
PCT Pub. Date: Apr. 19, 2012

(65) Prior Publication Data
US 2013/0289626 A1      Oct. 31, 2013

(51) Int. Cl.
*A61B 17/80* (2006.01)
*A61B 17/88* (2006.01)
*A61B 17/90* (2006.01)

(52) U.S. Cl.
USPC .............................. 606/280; 606/281; 606/96

(58) Field of Classification Search
USPC .................. 606/86 R, 96, 280, 281
See application file for complete search history.

(56) References Cited

U.S. PATENT DOCUMENTS

| 4,828,221 | A | 5/1989 | Scobie et al. |
| 5,364,399 | A | 11/1994 | Lowery et al. |
| 6,066,142 | A | 5/2000 | Serbousek et al. |
| 6,623,486 | B1 | 9/2003 | Weaver et al. |
| 7,316,687 | B2 | 1/2008 | Aikins et al. |
| 7,413,367 | B2 | 8/2008 | Hawang |
| 7,578,825 | B2 | 8/2009 | Huebner |
| 8,162,950 | B2 | 4/2012 | Digeser et al. |

(Continued)

FOREIGN PATENT DOCUMENTS

| EP | 2072016 A1 | 6/2009 |
| WO | 2005/092224 A1 | 10/2005 |
| WO | 2009121144 A1 | 10/2009 |

OTHER PUBLICATIONS

International Search Report and Written Opinion, PCT/US10/52425, dated Dec. 6, 2010.

(Continued)

*Primary Examiner* — Kevin T. Truong
*Assistant Examiner* — Christian Sevilla
(74) *Attorney, Agent, or Firm* — Lerner, David, Littenberg, Krumholz & Mentlik, LLP (57) ABSTRACT

An aiming block fixation system for fixing an aiming block to a bone plate includes a bone plate having an outer surface and a bone-contacting surface for application to a bone. The aiming block has an upper surface, a lower surface engageable with the outer surface of the bone plate. A first angled aiming block bore extending from the upper surface to the lower surface along an axis which is at a non-zero degree angle to an axis of a bone plate hole. A locking element extends through the angled aiming block bore and the bone plate hole such that a central longitudinal axis of the locking element is oriented at a non-zero degree angle to the first axis, with the locking element including a radially outwardly extending camming arm selectively engageable with a camming surface of the first bone plate hole.

22 Claims, 5 Drawing Sheets

(56) References Cited

U.S. PATENT DOCUMENTS

| | | |
|---|---|---|
| 2003/0040748 A1 | 2/2003 | Aikins et al. |
| 2005/0085818 A1 | 4/2005 | Huebner |
| 2005/0137606 A1 | 6/2005 | Binder et al. |
| 2005/0234472 A1* | 10/2005 | Huebner ............... 606/104 |
| 2007/0167953 A1 | 7/2007 | Prien et al. |
| 2008/0183172 A1 | 7/2008 | Fritzinger |
| 2009/0157086 A1* | 6/2009 | Digeser et al. ............... 606/96 |
| 2009/0228047 A1* | 9/2009 | Derouet et al. ............... 606/286 |
| 2010/0106196 A1 | 4/2010 | Erickson et al. |
| 2010/0179599 A1 | 7/2010 | Derouet et al. |
| 2011/0106086 A1 | 5/2011 | Laird |
| 2012/0078252 A1 | 3/2012 | Huebner et al. |
| 2012/0191104 A1 | 7/2012 | Jost et al. |
| 2012/0253347 A1 | 10/2012 | Murashko, Jr. |
| 2012/0271310 A1 | 10/2012 | McGee |

OTHER PUBLICATIONS

European Search Report for EP11184357 dated Jan. 19, 2012.

U.S. Notice of Allowance for U.S. Appl. No. 13/079,302, Patent No. 8,523,862, mailed May 1, 2013.

\* cited by examiner

BONE PLATE AIMING BLOCK

CROSS-REFERENCE TO RELATED APPLICATION

The present application is a national phase entry under 35 U.S.C. §371 of International Application No. PCT/US2010/052425 filed Oct. 13, 2010, published in English, incorporated herein by reference.

BACKGROUND OF THE INVENTION

The present invention relates to a bone plating system, instrumentation and method of use used in the fixation of fractures of long bones such as the femur, tibia, humerus and radius, including periarticular fractures. More specifically, the present invention encompasses an aiming block fixation system that aids in the location of bone screws and drilling of pilot holes for the placement and intraoperative adjustment and fixation of the plate to the fractured bone.

Typical fixation of a fracture of a long bone with a bone plate requires making an incision in the tissue, reducing the fracture, placing a bone plate on the fractured bone, and securing the bone plate to the bone with fixation elements such as screws. The bone plate immobilizes the fracture and keeps the bone in a correct position so as to allow the fracture to heal.

Typically, bone plates have a bone-contacting side and a side facing away from the bone with a plurality of holes or apertures extending between the two surfaces. These holes or apertures may be either threaded (for fixing the plate to the bone with locking screws) or non-threaded (for fixing the plate to the bone with regular screws) and may be circular or oblong in shape.

Such threaded screws are driven into the bone tissue after so-called pre-drilled or pilot-drilled holes have been generated in the bone tissue. These pre-drilled holes allow for a reliable screwing procedure whereby the risk of further destroying the bone with the screw is significantly reduced.

In order to facilitate the drilling of these pre-drilled holes there are known so-called aiming or targeting devices, which work like a drilling jig. Thereby, an aiming or targeting device is detachably fixed to the metal bone plate in a precise position.

One such bone plate is shown in U.S. Pat. No. 6,623,486 in which the plate has a head portion for placement adjacent the metaphysis of the bone and a shaft portion for placement against the diaphysis of the bone. The plate includes both locking (threaded) holes and non-locking holes. The locking holes are adapted to receive bone screws with threaded heads or proximal areas which engage the threads in the locking holes to thereby lock the screw to the plate. Bone screws without threaded heads can be then inserted into the non-locking holes or into the oblong holes which oblong holes permit the screws to be oriented at various angles.

Some types of bone plates, however, do not include threaded holes in a location that would accommodate the use of aiming or targeting devices. There thus exists a need for a system that will align a surgical tool (e.g., drill bit) with a hole of a bone plate in which the holes can be non-threaded. The present invention addresses this problem and others by providing an aiming block which has bores for aligning surgical tools, whose arrangement matches or corresponds to the arrangement of holes of a particular bone plate type. Given the lack of threaded holes in this particular bone plate type, the present invention provides a fixation system including a locking element which engages a surface surrounding a hole in the bone plate, whereby the aiming block is fixed to the bone plate.

BRIEF SUMMARY OF THE INVENTION

Various aspects of the present invention are achieved with an aiming block for a bone plate having bores therethrough for receiving bone screws, where such bores may be threaded or non-threaded. The bone plate has an outer surface and a bone-contacting surface. A camming surface may surround at least a first bore on the bone-contacting side of the bone plate and may be in a different plane than that of the bone-contacting lower surface. The camming surface could be a countersink in the bone contacting surface surrounding the bore.

The aiming block includes a first angled bore through which a locking element is inserted, and further includes a recess adjacent to a head on the locking element. The first bone plate bore and the first aiming block bore are angled with respect to each other at preferably 10 to 20°. The locking element head has an enlarged segment which engages the recess when the locking element is in a first rotational position and disengages in a second rotational position. The locking element extends through the angled aiming block bore and the first bone plate hole with which it aligns. An anti-rotation pin may extend through a second aiming block bore and a second bone plate bore to help prevent the aiming block from rotating with respect to the bone plate. The anti-rotation pin may have a smaller diameter than the locking element.

The locking element includes a shaft having the head and enlarged segment on a first end and a camming arm on a second end. The camming arm extends radially from the second end of the shaft at a non-zero degree angle to a central longitudinal axis of the shaft which is preferably coaxial with the axis of the aiming block bore. Rotation of the locking element to a second rotational position causes the camming arm to engage the camming surface around the first bone plate hole. The head of the locking element has a diameter larger than that of the first angled aiming block bore such that the aiming block is captured between the locking element head and the bone plate when the camming arm is engaged with the bone plate. The locking element head may include two enlarged segments along the central longitudinal axis, each having an enlarged radius compared to the shaft of the locking element. A first of these enlarged segments engages the recess in the aiming block when the locking element is in its first rotational position, thereby preventing the locking element from sliding out of the aiming block while the locking element's camming arm is not engaged with the bone plate. A second of these enlarged segments is thicker than the recess and will not enter the aiming block recess and thereby prevents the locking element from rotating past its second rotational position.

A method for fixing the aiming block to the bone plate using the locking element includes positioning the aiming block to align the first angled aiming block bore with the first bone plate bore. The locking element is inserted into the first angled aiming block bore and the first bone plate bore in a neutral rotational position (neither enlarged segment nor camming arm engaged) to allow it to be fully inserted without interference from the camming arm or the enlarged segments of the head. With the locking element head contacting the upper surface of the aiming block and the lower surface of the aiming block contacting the outer surface of the bone plate, the locking element is rotated to its second rotational position (preferably 180°) such that the locking element camming arm engages the camming surface around the first bone plate hole, thereby fixing the aiming block to the bone plate. A pin may be inserted through a second aiming block bore and a second bone plate bore into bone to prevent the aiming block from rotating with respect to the bone plate.

BRIEF DESCRIPTION OF THE DRAWINGS

FIG. 1b is a cross-sectional view along lines 1b-1b of 4a;

DETAILED DESCRIPTION

Figure 1:
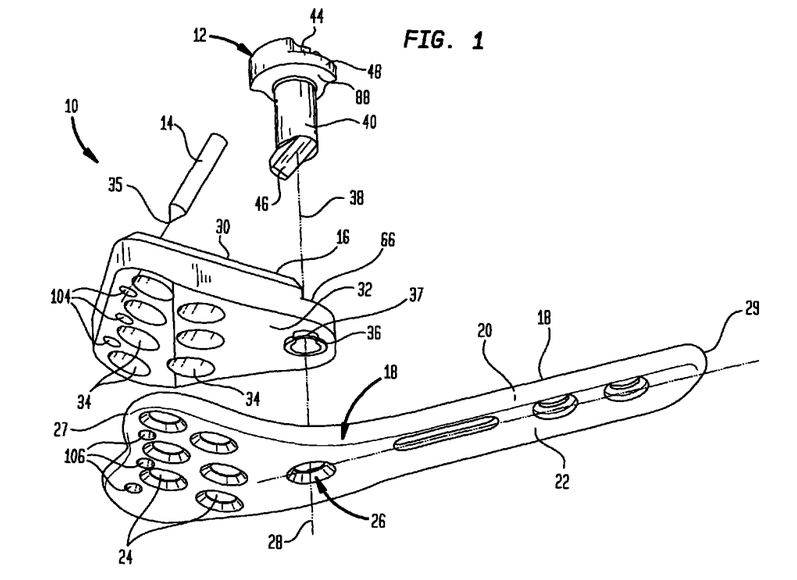
FIG. 1 is an exploded bottom perspective view of the aiming block fixation system of the present invention showing a locking element, a bone block and a bone plate.

Referring to FIG. 1 there is shown an exploded view of the instrumentation of the present invention generally denoted as 10. Instrumentation 10 includes a first locking element 12, a pin 14, and a drill guide block or aiming block 16. Also shown is a bone plate 18 including an outwardly facing surface 20 and a bone-contacting surface 22. Bone plate 18 may be angled to match the bone anatomy such as the distal radius as shown or at a joint end of a femur or tibia. The bone plate 18 also includes a plurality of bores 24 at one end thereof and a bone plate bore 26 spaced intermediate ends 27 and 29 of bone plate 18 along a longitudinal axis 29 thereof. Bone plate bore 26 has a central axis 28 which may be normal to the outer surface 20 bone plate 18. Bores 24 and 26 may have a frustroconical countersink therearound on the bone contacting surface 22 of bone plate 18. Plate 18 also includes a series of holes 106 which can receive bone pins.

Aiming block 16 includes an upper surface 30 and a lower surface 32. Aiming block 16 includes a plurality of bores 34 which are alignable with the bores 24 of the bone plate. When aligned, bores 24 and 34 extend along a first axis 35. Bores 34 are adapted to receive a surgical tool such as a drill so that pilot holes for bone screws may be drilled in the bone on which the bone plate 18 is to be mounted. Aiming block 16 has a specially designed angled bore 36 extending from a recessed surface 66 to surface 32 which is alignable with bone plate bore 26. Preferably, bore 26 is used so that the bone screws can be inserted into any or all the bores 24 without having to relocate locking element 12. It of course would be possible to locate bore 36 in alignment with one of bores 24 but this would require removing locking element 12 to drill a pilot hole through that bore. Angled bore 36 extends from an upper surface 30 of aiming block 16 to a lower surface 32 along a second axis 38 which is angled with respect to the central axis 28 of bore 26. Bore 36 includes an extension 37 the purpose of which will be discussed below.

Figure 1A:
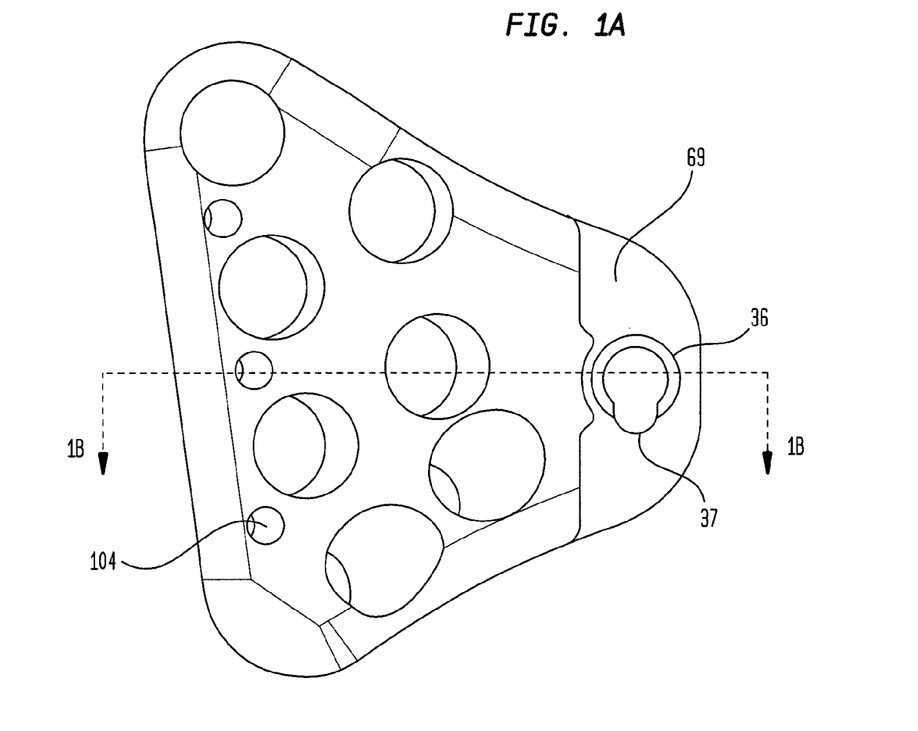
FIG. 1a is a top view of the aiming block shown in FIG. 1.
Figure 1B:
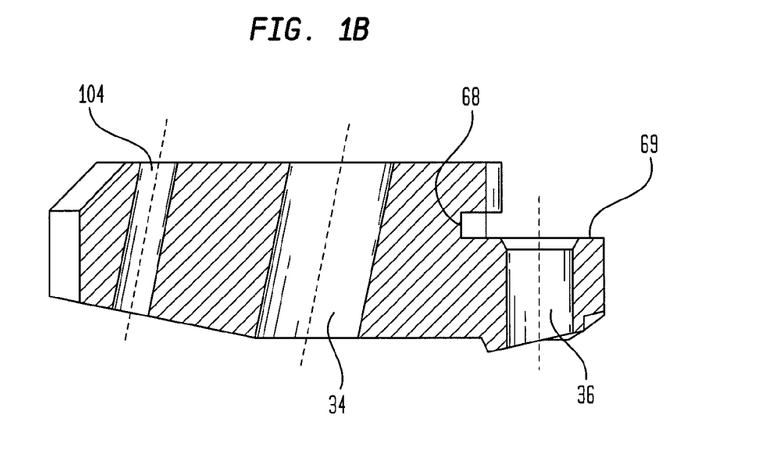

Referring to FIGS. 1a and 1b, there is shown aiming block 16 including bores 34 and 36 and bone extension 37. As can be seen in FIG. 1b, a covered slot 68 is formed partially around recessed surface 66.

Figure 2:
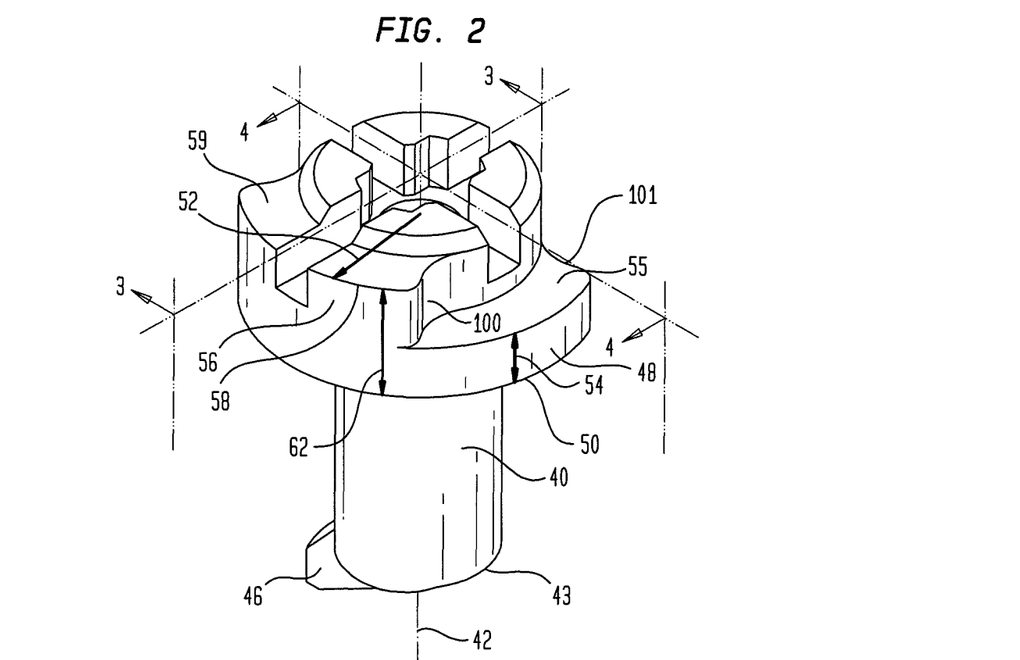
FIG. 2 is a perspective view of the locking element shown in FIG. 1.
Figure 3:
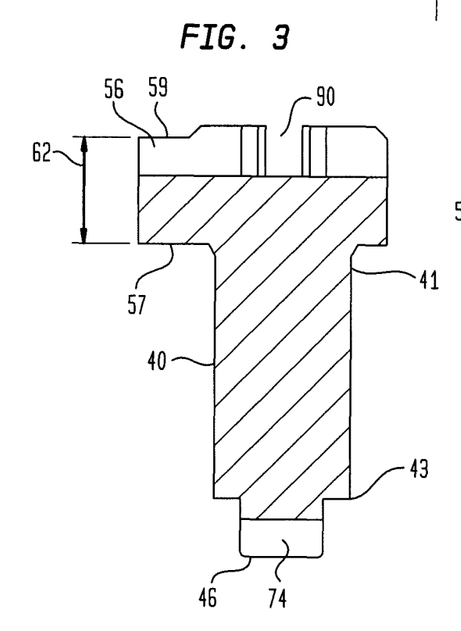
FIG. 3 is a cross-sectional view of the locking element of FIG. 2 along lines 3-3.
Figure 4:
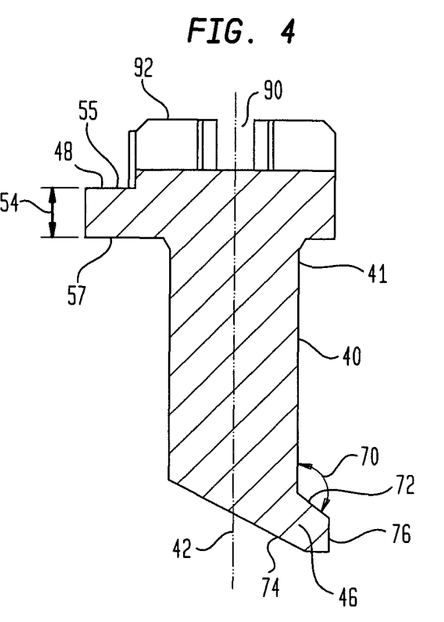
FIG. 4 is a cross-sectional view of the locking element shown in FIG. 2 along lines 4-4 oriented at 90 degrees from the cross-sectional view of FIG. 3.

Referring to FIGS. 2-4 there is shown locking element 12 which is insertable through bore 36 into bore 26 and having an end insertable into bore 26. Locking element 12 includes a shaft 40 having a central longitudinal axis 42. Upon insertion into bore 36, axis 42 is coaxial with axis 38 of bore 36. The shaft 40 has a first end 41 having a head 44 and a second end 43 having a camming arm 46 extending radially outwardly angled with respect to axis 42 away from shaft end 43. Head 44 includes a first enlarged segment 48 which extends outwardly from axis 42 and circumferentially over a first arc length 50 extending partially around the circumference of the head 44. Segment 48 and has a radius 52 which is larger than that of shaft 40. The first enlarged segment 48 has a first thickness 54 defined by an upper surface 55 and a lower surface 57. A surface 101 extends between the upper surface 55 and the lower surface 57. The head 44 further includes a second enlarged segment 56 which has a second arc length 58 extending from segment 48 partially around the circumference of the head 44 and has the same radius 52. The radii of the first and second enlarged segments could different with the second enlarged segment leading edge 100 spaced inwardly radially from a leading edge 101 of the first segment. The second enlarged segment 56 has a second thickness 62 defined by upper surface 59 and lower surface 57 which is greater than the thickness 54 of first segment 48. A surface 100 extends between the upper surface 59 of the second enlarged segment 56 and the upper surface 55 of the first enlarged segment 48. Either or both of the first and second enlarged segments 48, 56 may be in the form of flange extending radially outwardly perpendicular to the central longitudinal axis 42 of the locking element shaft 40.

The camming arm 46 has an upper surface 72 which extends radially outwardly from one end of the shaft at a non-zero degree angle 70 which preferably is 132 degrees to the central longitudinal shaft axis 42. Camming arm 46 has a lower surface 74 preferably extending at an angle of 154 degrees to axis 42. The camming arm 46, upper surface 72 and a lower surface 74 can be parallel to each other (have the same angle with respect to axis 42). The camming arm also includes an outer surface or tip 76 which can be parallel to the central longitudinal axis 42.

Figure 5:
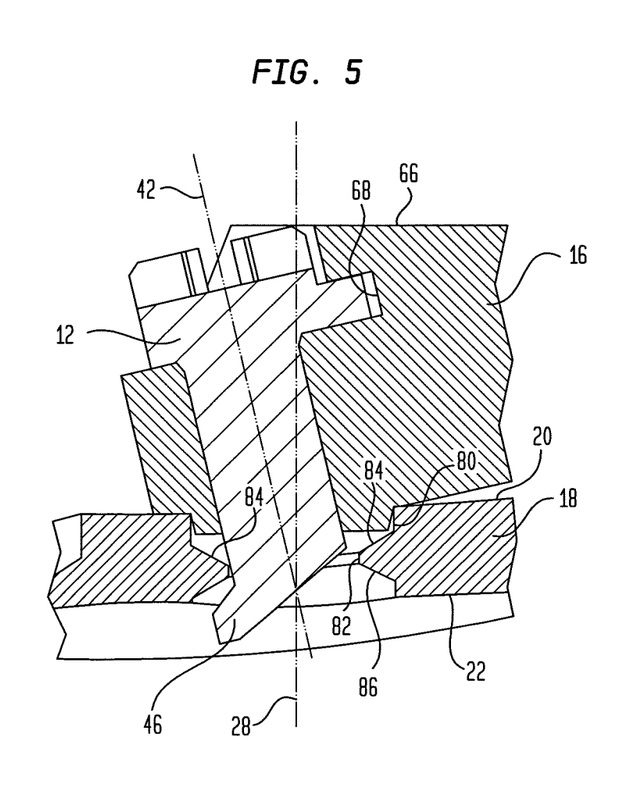
FIG. 5 is a partial cross-sectional view of the aiming block of FIGS. 1a and 1b including the locking element of FIGS. 2-4 located therein in a first position.
Figure 6:
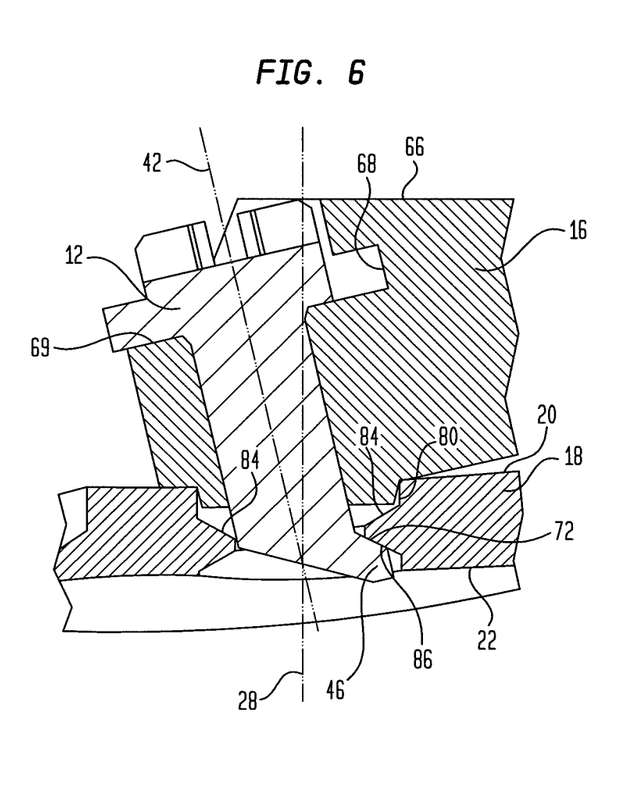
FIG. 6 is a cross-sectional view of FIG. 5 with the locking element rotated to a second rotational position.
Figure 7:
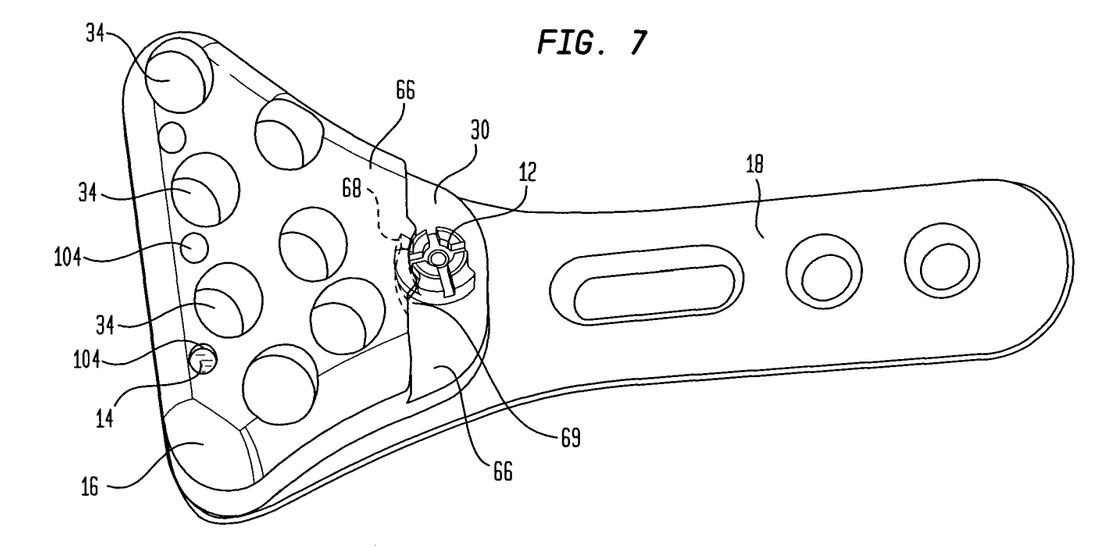
FIG. 7 is a top perspective view of the assembled aiming block, locking element and bone plate of FIG. 1.

Referring to FIGS. 5-7 there is shown partial cross-sectional views of the aiming block 16 mounted on the bone plate 18 utilizing the locking element 12. Note that one or more pins 14 preferably are inserted through one or more pin bores 104 in the aiming block and through one or more bores 106 in bone plate 18 into bone. Pins 14 are used to prevent rotation of the aiming block 16 with respect to the bone plate 18 when locked onto aiming block 16 by locking element 12. The upper surface 30 of the aiming block 16 includes portion 66 having covered slot 68 adjacent to the locking element head 44. The first thinner enlarged segment 48 engages the slot 68 when the locking element occupies a second rotational position as described below.

In a preferred embodiment best shown in FIGS. 5-6 the bone plate 18 includes first bore 26 having an inner wall 80 including a radially inwardly extending circumferential rib 82. Rib 82 can be formed by inwardly extending countersinks from both the outer and bone contacting surfaces. The bone-contacting surface 22 of the bone plate 18 surrounding the first bore 26 is recessed such that rib 82 is located intermediate the bone plate's outer surface 20 and bone-contacting surface 22. Rib 82 includes an upward-facing surface 84 and a bone-facing camming surface 86 of bone 26. As best seen in FIGS. 5-6 the upper surface 72 of the camming arm is angled such that it is engageable with the camming surface 86. In one embodiment, upper surface 72 is directed towards the bone at an angle of about 100° to 170° and preferably about 132° to the axis 42 of locking element 12. The dimensions and orientation of the camming arm 46 are designed according to the dimensions and orientation of surface 86 on the bone plate 18 with which the locking element is to be used. While the preferred embodiment includes a rib 82, the presence of such rib is not necessary. In the absence of a rib, the portion of the bone-contacting surface 22 of the bone plate 18 surrounding bone plate bore 26 would serve as the camming surface.

As best seen in FIGS. 5-6 the central longitudinal axis 42 of the locking element shaft 40 lies substantially along the second axis 38 and rotates substantially about this axis. When the aiming block 16 is mounted on the bone plate 18 the locking element's central longitudinal axis 42 is oriented at a non-zero degree angle to the first axis 28 of the first bone plate bore 26 or axis 35 of bore 24. This angle may be 10-20°. As shown in FIG. 5 the locking element 12 is inserted into the angled bore 36 and then into bone plate bore 26 in a neutral rotational position (without the camming arm or enlarged segment engaging the aiming block or bone plate) until a bottom surface 88 of the head 44 contacts the upper surface 30 of the aiming block 16. In this position the locking element 12 can slide axially in and out of the first angled bore 36 and bore extension 37 and through the bone plate hole 26 without interference between from the camming arm 46 or the first enlarged segment 48 of the head 44 and block 16. The locking element can then be rotated using a tool engaging slot 90 on head 44 to a first rotational position as shown in FIG. 5 in which the camming arm 46 is not engaged with the bone plate 18. In this position the first enlarged segment 48 of the head 44 engages the aiming block slot 68 to prevent the locking element 12 from sliding out of the angled bore 36. In order to fix the aiming block 16 to the bone plate 18, the locking element 12 is rotated to a second rotational position as shown in FIG. 6 in which upper surface 72 of the camming arm 46 engages camming surface 86 of bone plate 18. In this position the first enlarged segment 48 of head 44 is not engaged with aiming block slot 68. The second enlarged segment of the head 44 is oriented such that leading edge 100 contacts area 69 of the aiming block above recess 68 when the locking element 12 is rotated to its second rotational position. This interference prevents the locking element from rotating past its second position where camming arm 46 is engaged the bone plate camming surface 86. Preferably the rotational positions between neutral and engaged are 180° apart.

The neutral rotational position of the locking element 12 may corresponds to a rotational position intermediate the first rotational position and the second rotational position. In the neutral rotational position the camming arm 46 is not engaged with bone plate 18 and first enlarged segment 48 is not engaged with the aiming block above slot 68, thereby enabling the locking element 12 to freely slide in and out of angled bore 36 and bone plate bore 26. Locking element 12 must be in the neutral rotational position to be inserted or removed from angled bore 36 and the bone plate hole 26. When the locking element 12 is fully inserted into angled bore 36 and bone plate hole 26, locking element 12 may be rotated between its first and second rotational positions with the aid of one or more slots 90 in a top surface 92 of the head 44. Any means for driving a screw known in the art may be used in place of the one or more slots 90 such as a Phillips head or hex drive.

Although the use of the locking element according to the invention has been described in connection with the specific aiming block and bone plate of the invention, it will be apparent to those skilled in the art that it may be used advantageously with various other aiming blocks, bone plates, and implants.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An aiming block fixation system for fixing an aiming block to a bone plate comprising:
    a bone plate having an outer surface, a bone-contacting surface for application to a bone, first and second bone plate holes extending from the outer surface to the bone-contacting surface, and a camming surface surrounding the first bone plate hole at the bone-contacting surface, the first bone plate hole extending along a first axis;
    an aiming block having an upper surface, a lower surface engageable with the outer surface of the bone plate, a first angled aiming block bore extending from the upper surface to the lower surface along a second axis which is at a non-zero degree angle to the first axis of the first bone plate hole, the aiming block having an additional bore extending from the upper surface to the lower surface axially aligned with the second bone plate hole for guiding a surgical tool or bone screw therethrough; and
    a locking element extending through the first angled aiming block bore and the first bone plate hole such that a central longitudinal axis of the locking element is oriented at a non-zero degree angle to the first axis, with the locking element including a head having a bottom surface for bearing against the upper surface of the aiming block and a radially outwardly extending camming arm selectively engageable with the camming surface of the first bone plate hole such that the camming arm is disengaged when the locking element is in a first rotational position and engaged when in a second rotational position.

2. The aiming block fixation system as set forth in claim 1, wherein the second bone plate hole is non-threaded.

3. The aiming block fixation system as set forth in claim 1, wherein the camming surface of the bone plate is in a different plane than that of the bone-contacting surface of the bone plate.

4. The aiming block fixation system as set forth in claim 1, wherein the locking element has the head with a first enlarged segment extending radially with respect to the central longitudinal axis and the aiming block comprises a raised portion on the upper surface adjacent to the first angled aiming block bore with such raised portion having a recess having a height adjacent to the head on the locking element such that the first enlarged segment of the locking element head engages the recess as the locking element is rotated from the second rotational position to the first rotational position.

5. The aiming block fixation system as set forth in claim 4, wherein the locking element further comprises:
    a shaft with a first end and a second end;
    the head on the first end with the bottom surface having a diameter larger than that of the first angled aiming block bore such that the head is engageable with the upper surface of the aiming block; and
    the camming arm extending from the second end.

6. The aiming block fixation system as set forth in claim 5, wherein the locking element head first enlarged segment comprises
   a first radius greater than a radius of the head;
   a first arc length less than a full circumference of a circle having the first radius of such segment; and
   a first thickness defined along the central longitudinal axis less than the height of the aiming block recess.

7. The aiming block fixation system as set forth in claim 6, wherein the locking element head comprises a second enlarged segment having:
   a second radius greater than that of the head;
   a second arc length less than a full circumference of a circle having the second radius of such segment; and
   a second thickness defined along the central longitudinal axis.

8. The aiming block fixation system as set forth in claim 7, wherein the first and second enlarged segments of the locking element head are dimensioned such that:
   the first radius is equal to the second radius;
   the first arc length is equal to the second arc length; and
   the first thickness is less than the second thickness.

9. The aiming block fixation system as set forth in claim 7, wherein the second thickness is greater than the height of the recess.

10. The aiming block fixation system as set forth in claim 5, wherein the camming arm extends from the second end of the shaft at a non-zero degree angle to the central longitudinal axis of the locking element.

11. The aiming block fixation system as set forth in claim 10, wherein the locking element camming arm has a bottom surface in a plane oriented at a first non-zero degree angle to the central longitudinal axis of the locking element, and a top surface in a plane oriented at a second non-zero degree angle to the central longitudinal axis of the locking element.

12. The aiming block fixation system as set forth in claim 4, wherein the locking element is positioned through both the first angled aiming block bore and the first bone plate hole with the locking element head in contact with the upper surface of the aiming block, whereby the locking element is rotatable about its central longitudinal axis such that:
   in a neutral rotational position the camming arm is not engaged with the camming surface of the bone plate and the first enlarged segment of the head is not engaged with the recess in the aiming block;
   in the first rotational position the camming arm is not engaged with the camming surface of the bone plate but the first enlarged segment of the head is engaged with the recess in the aiming block; and
   in the second rotational position the camming arm is engaged with the camming surface of the bone plate but the first enlarged segment of the head is not engaged with the recess in the aiming block.

13. The aiming block fixation system as set forth in claim 11, wherein the camming arm top surface engages the camming surface of the bone plate to cause the aiming block to be pulled towards the bone plate with the aiming block being captured between the head of the locking element and the upper surface of the bone plate such that the aiming block is fixed to the bone plate.

14. A method for fixing an aiming block to a bone plate using a locking element, comprising:
   placing a bone plate having an outer surface, a bone-contacting surface and at least two bores extending from the upper surface to the lower bone-contacting surface, and a camming surface surrounding a first bore at the bone-contacting surface on a bone, the first bore extending along a first axis;
   placing an aiming block having an upper surface and a lower surface on the outer surface of the bone plate, the aiming block having a plurality of bores extending from the upper surface to the lower surface, the plurality of bores including a first angled aiming block bore extending from the upper surface to the lower surface along a second axis which is at a non-zero degree angle to the first axis of the first bone plate hole;
   aligning the first aiming block bore with the first bone plate bore;
   inserting a locking element through the first aiming block bore and the first bone plate bore along the second axis such that an axis of the locking element is oriented at a non-zero degree angle to the first axis, the locking element further having an end including a radially outwardly extending camming arm selectively engageable with the camming surface of the first bone plate bore; and
   rotating the locking element from a first rotational position where the camming arm is disengaged from the camming surface to a second rotational position where the camming arm is engaged with the camming surface.

15. The method as set forth in claim 14, wherein the bores in the bone plate are non-threaded.

16. The method as set forth in claim 14, wherein the camming surface of the bone plate is in a different plane than that of the bone-contacting lower surface of the bone plate.

17. The method as set forth in claim 14, wherein the aiming block comprises a raised portion on the upper surface adjacent to the first angled aiming block bore with such raised portion having a recess adjacent to a head on the locking element such that a first enlarged segment of the locking element head enters and engages the recess as the locking element is rotated to its first rotational position.

18. The method as set forth in claim 14, further comprising:
   positioning the aiming block to align the first angled aiming block bore with the first bone plate bore, and to align two additional aiming block bores with two additional bone plate bores;
   inserting the locking element in a neutral rotational position through the first angled aiming block bore and the first bone plate bore;
   inserting a pin through a second aiming block bore and a second bone plate bore; and
   rotating the locking element to its second rotational position with the head of the locking element being in contact with the upper surface of the aiming block, such that the camming arm engages the camming surface of the first bone plate bore.

19. A bone plate targeting system, comprising:
   a bone plate having a plurality of through bores;
   an outer surface and a bone contacting surface;
   an aiming block engaging the outer surface of the bone plate, the aiming block having an upper surface, a first bore axially aligned with a first bone plate through bore, and a second aiming block hole having an axis angularly offset from the axis of a second bore in the bone plate, the first and second bone plate bores alignable with the respective first and second aiming block bores; and
   a locking element extending through the second aiming block bore and the second bone plate bore, the locking element including a central longitudinal axis and a head having a bottom surface for bearing against the upper surface of the aiming block, the locking element having a radially outwardly extending camming arm including a camming arm surface for engaging the bone plate in a first rotational position and disengaging from the bone plate in a second rotational position.

20. The aiming block fixation system as set forth in claim 19, wherein the locking element has the head with a first enlarged segment extending radially with respect to the central longitudinal axis and the aiming block comprises a raised portion on the upper surface adjacent to the first angled aiming block bore with such raised portion having a recess having a height adjacent to the head on the locking element such that the first enlarged segment of the locking element head engages the recess as the locking element is rotated from the second rotational position to the first rotational position.

21. The aiming block fixation system as set forth in claim 20, wherein the camming arm extends from the second end of a shaft at a non-zero degree angle to the central longitudinal axis of the locking element.

22. The aiming block fixation system as set forth in claim 21, wherein the locking element camming arm has a bottom surface in a plane oriented at a first non-zero degree angle to the central longitudinal axis of the locking element, and a top surface in a plane oriented at a second non-zero degree angle to the central longitudinal axis of the locking element.

* * * * *